United States Patent
Kuppurathanam et al.

(10) Patent No.: US 8,353,943 B2
(45) Date of Patent: Jan. 15, 2013

(54) VARIABLE WEAVE GRAFT WITH METAL STRAND REINFORCEMENT FOR IN SITU FENESTRATION

(75) Inventors: Shyam Kuppurathanam, Bloomington, IN (US); David P. Biggs, Bloomington, IN (US); Krasnodar Ivancev, Hampstead (GB); Peter Harris, Flaunden (GB)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/542,336

(22) Filed: Aug. 17, 2009

(65) Prior Publication Data

US 2010/0161025 A1 Jun. 24, 2010

Related U.S. Application Data

(60) Provisional application No. 61/092,996, filed on Aug. 29, 2008.

(51) Int. Cl.
*A61F 2/82* (2006.01)
(52) U.S. Cl. ........................................ 623/1.1; 623/1.36
(58) Field of Classification Search ........................ None
See application file for complete search history.

(56) References Cited

U.S. PATENT DOCUMENTS

| | | | |
|---|---|---|---|
| 4,352,358 A | 10/1982 | Angelchik | 128/334 |
| 5,984,955 A | 11/1999 | Wisselink | 623/1 |
| 5,989,287 A | 11/1999 | Yang et al. | 623/1 |
| 6,019,786 A | 2/2000 | Thompson | |
| 6,161,399 A | 12/2000 | Jayaraman | |
| 6,187,033 B1 | 2/2001 | Schmitt et al. | 623/1 |
| 6,192,944 B1 * | 2/2001 | Greenhalgh | 139/425 R |
| 6,221,099 B1 | 4/2001 | Andersen | |
| 6,371,981 B1 | 4/2002 | Yang et al. | 623/1.13 |
| 6,395,018 B1 | 5/2002 | Castaneda | 623/1.13 |
| 6,432,131 B1 | 8/2002 | Ravenscroft | 623/1.13 |
| 6,524,335 B1 | 2/2003 | Hartley et al. | 623/1.13 |
| 6,576,007 B2 | 6/2003 | Dehdashtian et al. | 623/1.13 |
| 6,648,913 B1 | 11/2003 | Yee et al. | 623/1.35 |
| 6,792,979 B2 | 9/2004 | Konya et al. | |
| 6,814,754 B2 | 11/2004 | Greenhalgh | |
| 6,949,121 B1 | 9/2005 | Laguna | 623/1.35 |
| 7,037,329 B2 | 5/2006 | Martin | 623/1.13 |
| 7,393,357 B2 | 7/2008 | Stelter et al. | |

(Continued)

FOREIGN PATENT DOCUMENTS

EP 1 097 728 A1 5/2001

(Continued)

OTHER PUBLICATIONS

PCT International Search Report from PCT/US2009/004829 dated Nov. 24, 2009.

(Continued)

*Primary Examiner* — Thomas J Sweet
*Assistant Examiner* — Rebecca Preston
(74) *Attorney, Agent, or Firm* — Brinks Hofer Gilson & Lione

(57) ABSTRACT

The disclosure relates to an implantable woven graft for bridging a defect in a main vessel near one or more branch vessels. The graft includes a region of reduced density. Reduced density regions are alignable with at least one of the one or more branch vessels, and are suitable for in situ fenestration, for example by perforation. The disclosed examples are particularly suited for bridging abdominal aortic aneurysms.

18 Claims, 7 Drawing Sheets

U.S. PATENT DOCUMENTS

| | | |
|---|---|---|
| 7,407,509 B2 | 8/2008 | Greenberg et al. |
| 7,550,004 B2 | 6/2009 | Bahler et al. |
| 2001/0027338 A1 | 10/2001 | Greenberg ............... 623/1.13 |
| 2001/0041927 A1 | 11/2001 | Solem ..................... 623/1.13 |
| 2002/0034902 A1 | 3/2002 | Litton |
| 2002/0042644 A1 | 4/2002 | Greenhalgh |
| 2002/0052649 A1* | 5/2002 | Greenhalgh ............. 623/1.35 |
| 2002/0068967 A1* | 6/2002 | Drasler et al. ........... 623/1.13 |
| 2002/0082674 A1 | 6/2002 | Anson et al. ............. 623/1.13 |
| 2003/0130719 A1 | 7/2003 | Martin ..................... 623/1.13 |
| 2003/0135265 A1* | 7/2003 | Stinson ................... 623/1.16 |
| 2003/0204235 A1 | 10/2003 | Edens et al. |
| 2004/0059406 A1 | 3/2004 | Cully |
| 2004/0133266 A1* | 7/2004 | Clerc et al. .............. 623/1.22 |
| 2004/0193177 A1 | 9/2004 | Houghton et al. |
| 2004/0215320 A1 | 10/2004 | Machek |
| 2004/0254627 A1 | 12/2004 | Thompson et al. ...... 623/1.11 |
| 2005/0004654 A1 | 1/2005 | Khosravi et al. ......... 623/1.13 |
| 2005/0137677 A1 | 6/2005 | Rush |
| 2005/0154444 A1 | 7/2005 | Quadri |
| 2005/0177225 A1 | 8/2005 | Hunter et al. |
| 2005/0187604 A1 | 8/2005 | Eells et al. |
| 2005/0222668 A1 | 10/2005 | Schaeffer et al. |
| 2005/0240261 A1 | 10/2005 | Rakos et al. |
| 2005/0273162 A1 | 12/2005 | Laguna .................... 623/1.53 |
| 2006/0009835 A1 | 1/2006 | Osborne et al. |
| 2006/0019561 A1 | 1/2006 | Schindzielorz et al. |
| 2006/0024496 A1 | 2/2006 | Hietpas et al. |
| 2006/0095118 A1 | 5/2006 | Hartley ................... 623/1.35 |
| 2006/0129225 A1 | 6/2006 | Kopia et al. |
| 2006/0155359 A1 | 7/2006 | Watson ................... 623/1.13 |
| 2006/0247760 A1 | 11/2006 | Ganesan et al. ......... 623/1.16 |
| 2006/0253190 A1 | 11/2006 | Kuo |
| 2007/0010874 A1 | 1/2007 | Sun ......................... 623/1.35 |
| 2007/0219619 A1* | 9/2007 | Dieck et al. ............. 623/1.13 |
| 2008/0114444 A1 | 5/2008 | Yu |
| 2009/0259290 A1 | 10/2009 | Bruszewski et al. ..... 623/1.13 |

FOREIGN PATENT DOCUMENTS

| | | |
|---|---|---|
| WO | WO 97/25002 A1 | 7/1997 |
| WO | WO 97/33532 | 9/1997 |
| WO | WO 00/78250 A1 | 12/2000 |
| WO | WO 02/35988 A2 | 5/2002 |
| WO | WO 03/065933 | 8/2003 |
| WO | WO 2006/036690 | 4/2006 |
| WO | WO 2007/028112 | 3/2007 |
| WO | WO 2008/112242 A2 | 9/2008 |

OTHER PUBLICATIONS

PCT Written Opinion from PCT/US2009/004829 dated Nov. 24, 2009.

Non-Final Office Action in U.S. Appl. No. 12/136,857 dated Aug. 16, 2010, 8 pages.

Final Office Action in U.S. Appl. No. 12/136,857 dated Apr. 6, 2011, 10 pages.

Non-Final Office Action in U.S. Appl. No. 12/136,857 dated Nov. 7, 2011, 14 pages.

Non-Final Office Action in co-pending U.S. Appl. No. 12/233,359 dated Aug. 13, 2010, 10 pages.

International Search Report—PCT/US2008/008922; Filing Date Jul. 23, 2008, 6 pages.

* cited by examiner

VARIABLE WEAVE GRAFT WITH METAL STRAND REINFORCEMENT FOR IN SITU FENESTRATION

PRIORITY CLAIM

This application claims the benefit of provisional U.S. Patent Application Ser. No. 61/092,996, filed Aug. 29, 2008, which is incorporated herein by reference in its entirety.

BACKGROUND OF THE INVENTION

Aneurysms occur in blood vessels in locations where, due to age, disease or genetic predisposition, the blood vessel strength or resiliency is insufficient to enable the blood vessel wall to retain its shape as blood flows therethrough, resulting in a ballooning or stretching of the blood vessel at the limited strength/resiliency location to thereby form an aneurysmal sac. If the aneurysm is left untreated, the blood vessel wall may continue to expand, to the point where the remaining strength of the blood vessel wall is below that necessary to prevent rupture, and the blood vessel will fail at the aneurysm location, often with fatal result.

To prevent rupture, a stent graft of a tubular construction may be introduced into the blood vessel, for example intraluminally. Typically, the stent graft is deployed and secured in a location within the blood vessel such that the stent graft spans the aneurysmal sac. The outer surface of the stent graft, at its opposed ends, is sealed to the interior wall of the blood vessel at a location where the blood vessel wall has not suffered a loss of strength or resiliency. Blood flow in the vessel is thus channeled through the hollow interior of the stent graft, thereby reducing, if not eliminating, any stress on the blood vessel wall at the aneurysmal sac location. Therefore, the risk of rupture of the blood vessel wall at the aneurysmal location is significantly reduced, if not eliminated, and blood can continue to flow through to the downstream blood vessels without interruption.

In many cases, however, the damaged or defected portion of the vasculature may include a branch vessel. For example, in the case of the abdominal aorta, there are at least three branch vessels, including the celiac, mesenteric, and renal arteries, leading to various other body organs. Thus, when the damaged portion of the vessel includes one or more of these branch vessels, some accommodation must be made to ensure that the stent graft does not block or hinder blood flow through the branch vessel.

A common method to provide continued blood flow to branch vessels includes by-pass vessels surgically located in an undamaged region of the aorta that is not stented. Such invasive methods, however, are undesirable. A less invasive technique to provide continued blood flow to branch vessels includes the placement of holes or fenestrations in the stent graft that are aligned with the side branch vessel so as to allow blood to continue to flow into the side branch vessel. The fenestration approach is the preferred method since it does not involve major vascular surgery. However, inaccuracies in the location of fenestrations may occur due to the unique vasculature and location of branch vessels in each patient.

SUMMARY

In one example, an implantable prosthesis is provided. The implantable prosthesis comprises a graft body forming a lumen with a proximal end and a distal end. At least a portion of the lumen is defined by a woven fabric comprising textile strands and metal strands aligned in a first direction interwoven with textile strands and metal strands aligned in a second direction. The woven fabric further comprises a main portion and at least one reduced density region. The main portion has a weave density that is greater than the weave density of the reduced density region. The metal strands are interwoven in at least the main portion and aligned with the reduced density region.

In another example, an implantable prosthesis for treatment of a main vessel defect near one or more branch vessels is provided. The prosthesis comprises a graft comprising textile strands aligned in a first direction interwoven with textile strands and metal strands aligned in a second direction. The woven strands define a lumen with a proximal end and a distal end. The graft further comprises a main portion and at least one passage disposed between the proximal and distal end. The metal strands are aligned with the at least one passage and woven in at least the main portion. Although at least some textile strands traverse the at least one passage, the passage is defined by having a lower weave density than the main portion.

In a further example, a method of bridging a defect in a main vessel near at least one branch vessel is provided. The method comprises providing a prosthesis comprising at least one stent and an implantable variable weave graft comprising textile strands and metal strands aligned in a first direction interwoven with textile strands and metal strands aligned in a second direction, the woven strands defining a lumen with a main portion and at least one reduced density region. The reduced density region has a weave density lower than the main portion weave density. The metal strands are aligned with the reduced density region and woven in at least the main portion. The prosthesis is deployed into the main vessel of a patient in need thereof, such that a reduced density region is aligned with a branch vessel. The reduced density region may be perforated to define a passageway from the main vessel to the at least one branch vessel.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

Figure 1:
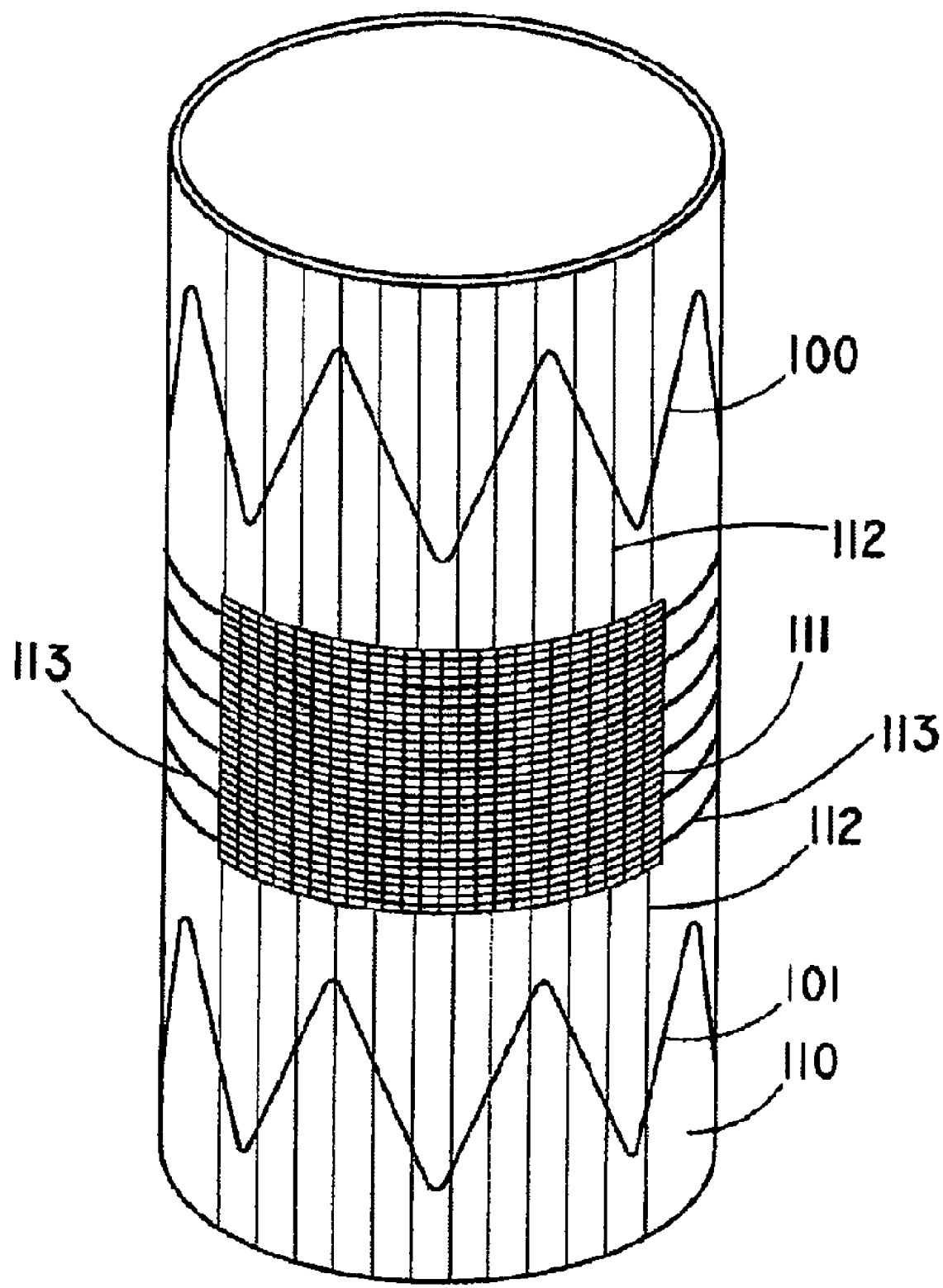
FIG. 1 is a perspective illustration of one example of a variable weave graft according to the present disclosure.

The present disclosure provides for a variable weave graft having a reduced density region for bridging a defect in a main vessel near one or more branch vessels. Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, billiary, urethral and ureteral passages.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The terms "about" or "substantially" used with reference to a quantity includes variations in the recited quantity that are equivalent to the quantity recited, such as an amount that is insubstantially different from a recited quantity for an intended purpose or function.

The term "stent" means any device or structure that adds rigidity, expansion force, or support to a prosthesis.

The term "alloy" refers to a substance composed of two or more metals or of a metal and a nonmetal intimately united, such as by chemical or mechanical interaction. Alloys can be formed by various methods, including being fused together and dissolving in each other when molten, although molten processing is not a requirement for a material to be within the scope of the term "alloy."

The term "stent graft" as used herein refers to a prosthesis comprising a stent and a graft material associated therewith that forms a lumen through at least a portion of its length.

"Proximal" means that position or portion of a component which is closest to the patient's heart.

"Distal" means that position of portion of a component which is furthest from the patient's heart.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "strand" as used herein is a generic term for a continuous strand of material suitable for weaving. For example, strands may include, but are not limited to monofilaments, filaments twisted together, fibers spun together or otherwise joined, yarns, roving yarns, crepe yarns, ply yarns, cord yarns, threads, strings, filaments laid together without twist, as well as other configurations.

Variable Weave Grafts

Variable weave grafts of the present disclosure include any prosthesis that is introduced temporarily or permanently into the body for the prophylaxis or therapy of a medical condition. Typical subjects (also referred to herein as "patients") are vertebrate subjects (i.e., members of the subphylum cordata), including, mammals such as cattle, sheep, pigs, goats, horses, dogs, cats and humans. Variable weave grafts of the present disclosure comprise at least one region of reduced density permitting in situ fenestration.

For example, FIG. 1 depicts one example of a segment of an illustrative stent graft comprising stents 100, 101 and variable weave graft 110. The variable weave graft 110 comprises a weave of textile strands aligned in a first direction interwoven with textile strands aligned in a second direction. Though FIG. 1 depicts the strands aligned in the first direction perpendicular to the strands aligned in the second direction, the strands in the first direction and second direction may have any suitable orientation. The graft 110 further comprises a reduced density region 111. The reduced density region 111 comprises a weave density that is lower than the weave density of the remaining, or main, portion of the variable weave graft 110. Metal strands 112, 113 may be interwoven with the textile strands in at least the main portion and aligned with the reduced density region 111. The metal strands 112, 113 assist in forming a tighter structure around a stent, for example a bridge stent, deployed through the reduced density region 111 after it is perforated in situ, for example by a guidewire. The metal strands 112, 113 also reinforce the fenestrated created by the perforation of the reduced density region 111, thereby reducing possible fluid leakage.

In one example, stents are located adjacent the reduced density graft region 111 for support and rigidity. For example, stents may be distal 101 and proximal 100 the reduced density region 111.

Figure 2:
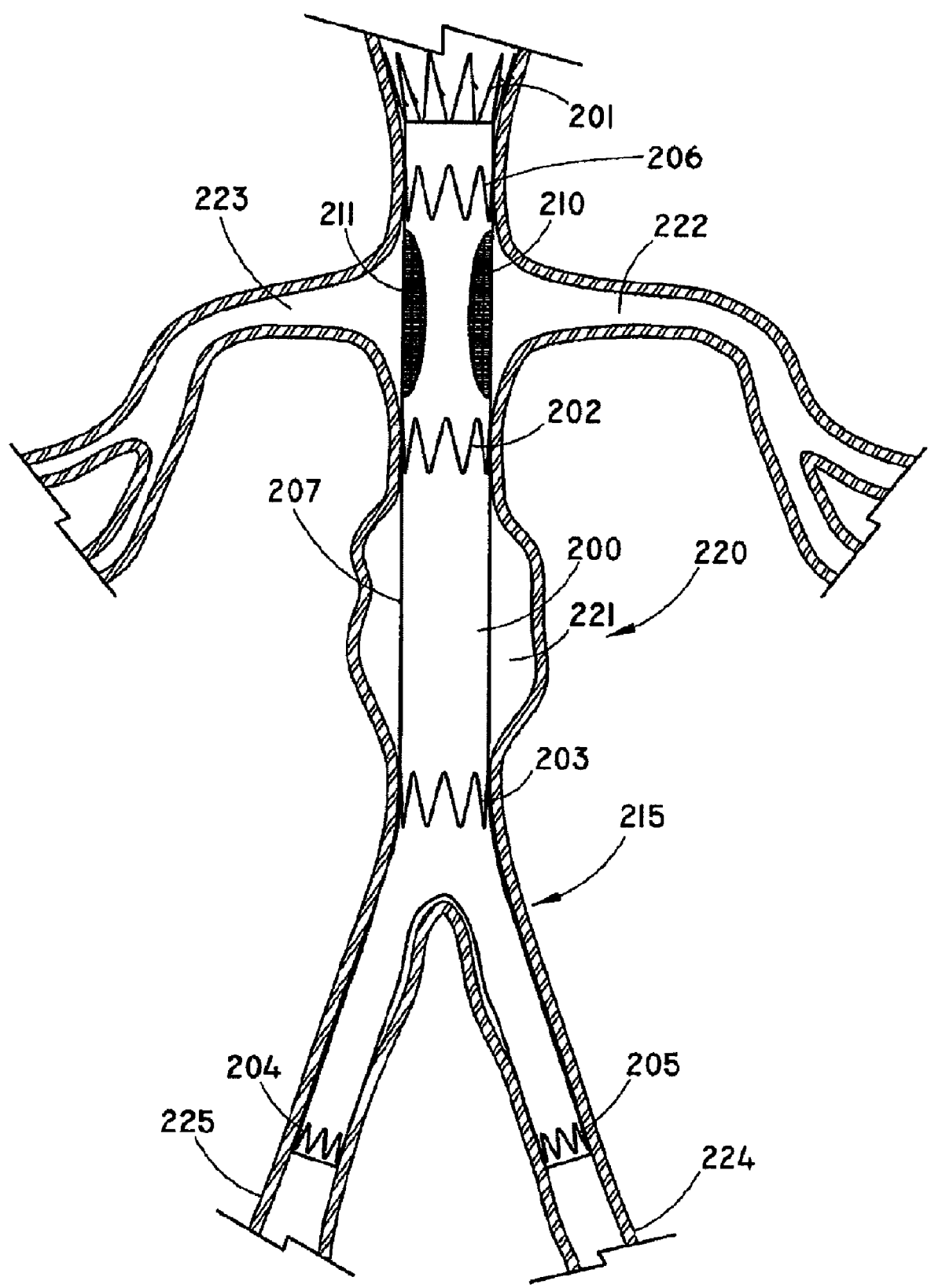
FIG. 2 depicts an abdominal aorta with a variable weave graft having reduced density regions aligned with the renal arteries.

The reduced yarn density region of the variable weave graft is preferably aligned with a branch vessel upon implantation. For example, FIG. 2 illustrates an aortic stent graft 200 comprising a main portion 207 and two reduced density regions 210, 211 aligned with the renal arteries 222, 223. The aorta 220 has an aneurysm 221 between the renal arteries 222, 223 and the iliac arteries 224, 225. Upon implantation, the reduced density regions 210, 211 are aligned with the renal arteries 222, 223, respectively. The reduced density regions may be perforated, preferably in situ, to establish fenestrations providing blood flow to the real arteries 222, 223.

For example, in situ fenestrations may be created within the reduced density regions to permit blood flow therethrough by any suitable means, including, but not limited, to the insertion of a guide wire, balloon, and/or stent to perforate the reduced density region. In one example, a variable weave graft comprising a reduced density region may be delivered and positioned at a desired location within a patient's vasculature via a guide wire. Following proper positioning of the graft, the guide wire may be used to poke through and perforate the reduced density region. In some examples, an inflatable balloon may be used to enhance perforation of the reduced density region to further enable blood flow through the fenestration.

Metal strands may reinforce the perforation of the reduced density thereby reducing possible blood leakage. For example, metal strands may prevent the perforation of the reduced density region from expanding beyond the reduced density region. In some examples, a stent such as a bridge stent or covered stent is deployed through the perforation of the reduced density region to assist blood flow to branch vessels. Metal strands may assist the graft in forming a tighter structure around the bridge stent deployed through the perforation of the reduced density region, thereby reducing blood loss. In one example the metal strands terminate about the periphery of the reduced density region. The metal strands abut the reduced density region and do not traverse the reduced density region. The metal strand ends retain the bridge stent from over expansion and prevent the graft weave from unraveling. Alternatively, at least some of the metal strands may traverse the reduced density region partially or completely. Metal strands traversing the reduced density region also limit undesirable expansion of the bridge stent and perforation in the reduced density region.

Figure 3:
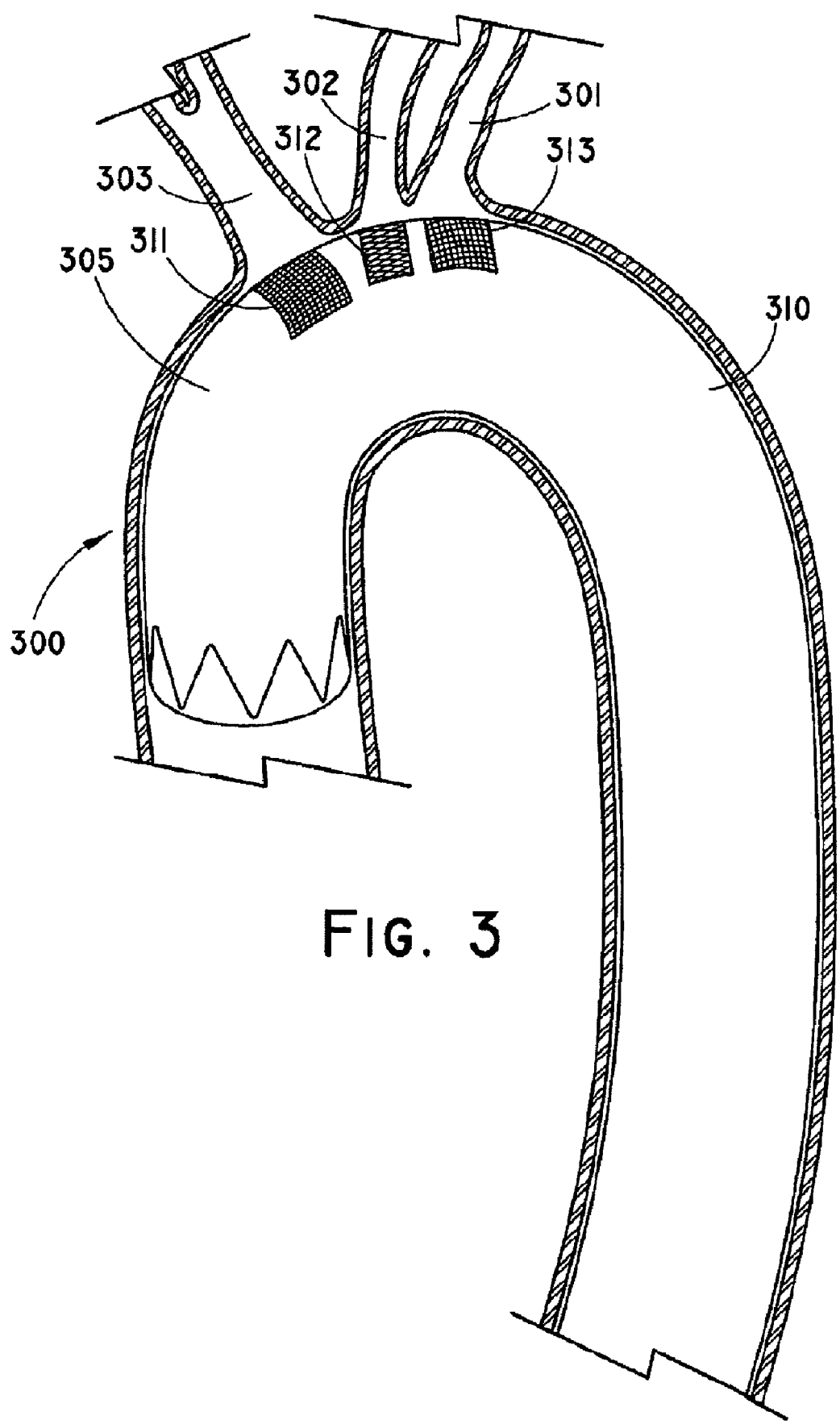
FIG. 3 depicts a variable weave graft positioned in the thoracic aorta and having reduced density regions aligned with the cranial arteries.
Figure 4:
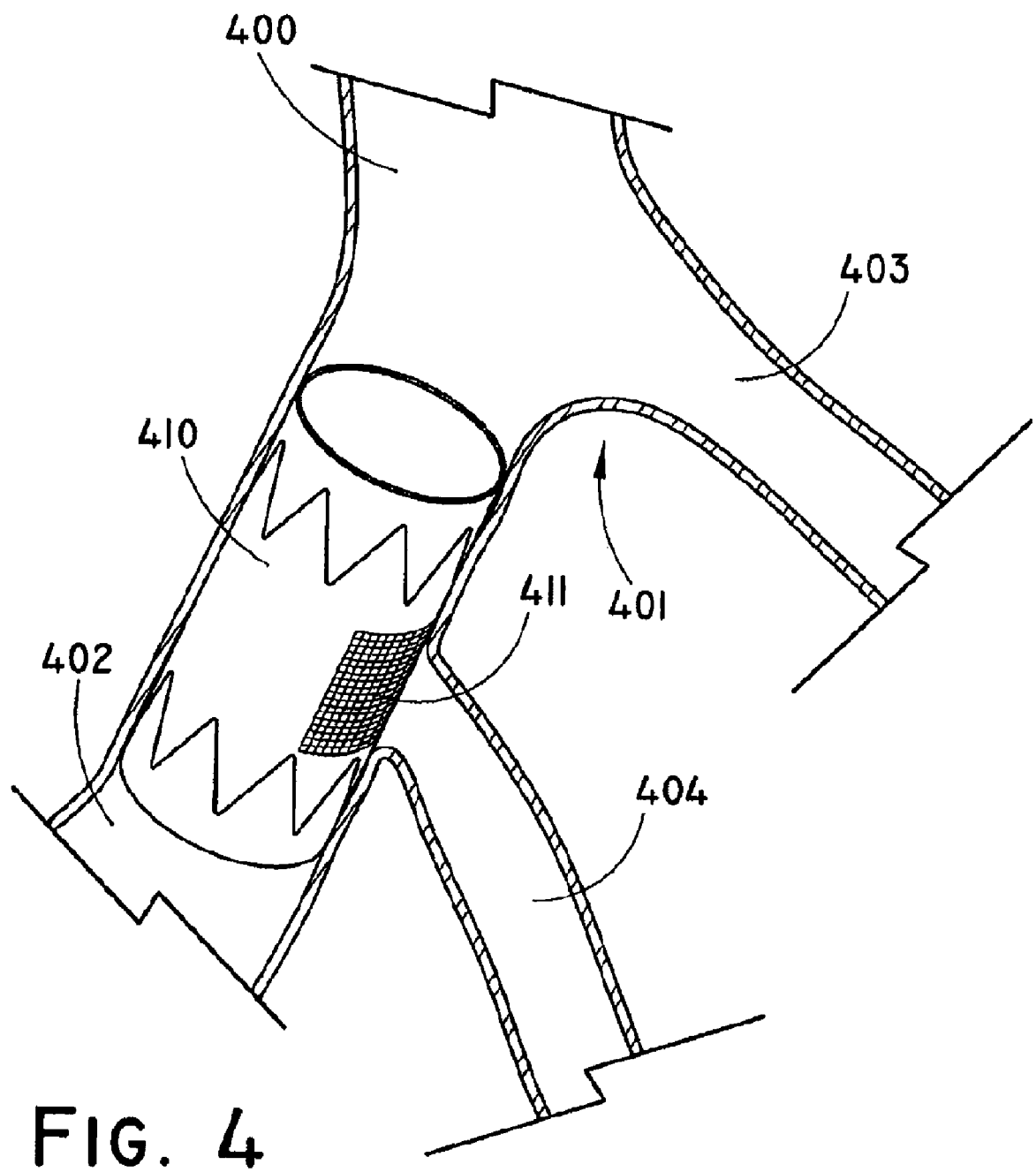
FIG. 4 is a partial illustration of the abdominal aorta with a variable weave graft according to the present disclosure placed in the iliac artery and having a reduced density region aligned with the hypogastric artery.

FIGS. 3 and 4 further illustrate stent grafts having reduced density regions aligned with various vessels that branch off the aorta. For example, FIG. 3 illustrates a variable weave graft 310, implanted within the thoracic aorta 300, having a main graft portion 305 and reduced density regions 311, 312, 313 aligned with the left subclavian artery 301, the left common carotid artery 302, and the brachiocephalic trunk 303. FIG. 4 is a partial illustration of an aortic vessel 400 at the point of bifurcation 401 into the iliac arteries 402, 403. As depicted, a stent graft 410 having a generally tubular shape is implanted within the left iliac artery 402 with a reduced density region 411 aligned with the hypogastric artery 404.

Though the above examples illustrate grafts located within the aorta, prostheses of the present disclosure may be implanted in any body vessel, including main vessels in which one or more branch vessels may be located. Though reduced density regions in the illustrative figures above are shown with rectangular or round shapes, the shape and size of the reduced yarn density region may be any appropriate size and shape. For example, the reduced density region may comprise a square shape, a polygonal shape, or be free-form. Furthermore, the reduced density region may have any suitable length and width. For example, the reduced density region may have a width which is less than the circumferential width (e.g., partial circumference) or be circumferentially around the variable weave graft.

Graft Weaves

The graft may comprise any kind of suitable weave or weaves patterns. For example, the variable weave graft may include, but is not limited to, weave patterns such as plain weaves, modified plain weaves, basket weaves, rep or rib weaves, twill weaves (e.g., straight twill, reverse twill, herringbone twill), modified twill weaves, satin weaves, double weaves (e.g., double-width, tubular double weave, reversed double weave), and any other related weave patterns. The reduced density region of the variable weave graft may comprise a similar weave pattern or a different weave pattern from the remainder of the graft. In one example, the variable weave graft comprises a single weave pattern for both the main portion and reduced density region. In another example, the variable weave graft comprises two or more weave patterns for the main portion and reduced density region of the graft.

The graft reduced density region may be woven, for example, by dropping and adding textile strands and metallic strands, by fast/slow take-up, and by having more than one weave patterns and designs. In one example, the variable weave graft comprises a plain weave of textile strands. The plain weave has 150 ends per inch and 250 picks per inch. An "end" refers to an individual warp strand, and "sett" is the number of warp strands per inch in a woven fabric. A "pick" refers to an individual weft strands, and "pick count" is the number of weft strands per inch in a woven fabric. The reduced density region also comprises a plain weave of textile strands having 150 ends per inch. To be susceptible to perforation, the reduced density region textile strand pick count is less than 150, allowing the region to have a textile strand density less than that of the main portion of the graft.

Preferably, the reduced density region textile strand pick count is between about 10% to about 90% of the textile strand pick count of the main portion of the graft. Even more desirably, the reduced density region textile strand pick count is between about 15% to about 30% of the main portion textile strand pick count.

In another example, the textile strand sett may be reduced in the reduced density region as compared to the textile strands in the graft main portion. Desirably, the reduced density region textile strand sett is between about 10% to about 90% of the graft main portion. Even more desirably, the reduced density region textile strand sett is between 15% to about 35% of the graft main portion.

The reduced density region textile strand pick count and sett may vary depending on a number of factors, including intended use of the variable weave graft, the selected weave or weave patterns, and the weave density of the graft main portion. In one example, the reduced density region may include a variable textile strand weave density. For example, the reduced density region may have a higher textile strand weave density about the circumference of the reduced density region and progressively lessen as the weave approaches the center of the reduced density region. As used here, the circumference may include a perimeter region such as that shown in FIG. 5A and indicated by reference numeral 501. A reduced density region variable textile strand weave may permit a tighter fit between a bridge stent and a perforation, thereby decreasing any fluid leakage about the circumference of the perforation.

The reduced density region may have any suitable shape, including but not limited to round, obround, polygonal, rectangular, square, or freeform, or combinations thereof. In one example, the reduced region may be woven in a circular fashion, thereby permitting a bridge stent to better conform to the perforation, and ultimately the fenestration.

Metal strands are woven in the variable weave graft and aligned with the reduced density regions. In one example, the metal strands are woven only in the graft main portion, terminating at and abutting the reduced density region. The reduced density region comprises a weave of only textile strands as the metal strands do not traverse the reduced density region. The metal strands may be woven, for example, by dropping and adding strands adjacent the reduced density region. For example, warp and/or weft metal strands are threaded into a loom together with the textile strands comprising the variable weave graft. The warp and/or weft metal strands are woven together with the textile strands in the graft main portion. At an area abutting the reduced density region, the warp and/or weft metal strands are dropped, and subsequently added following the completion of weaving the textile strands in the reduced density region to which the metal strands in the main portion are aligned.

In another example, at least some of the metal strands at least partially traverse the reduced density region. For example, the metal strands may comprise a variable weave within the reduced density region. In one example, the center of the reduced density region includes a reduced density of metal strands. The metal strands are woven such that the metal strand density gradually increases as the weave moves from the reduced density region center to the periphery of the reduced density region. This may permit for easier perforation about the center of the reduced density region as well as improved sealing about the periphery of the reduced density region by reducing overexpansion of the perforated fenestration.

In addition to weaving, the graft may be constructed by knitting or braiding metal strands, or any other suitable process. For example, the graft may be knit or braid together Nitinol wires and polyester fibers (e.g., not only by adding Nitinol in a traverse fashion).

Graft Material

The graft material may comprise textile strands and metal strands. Textile strands may comprise any biocompatible material suitable for weaving.

The textile strands may be natural, synthetic, or manufactured. For example, biocompatible materials include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile graft, provided the final textile is biocompatible.

Polymeric materials suitable for textile strands include polyethylene, polypropylene, polyaramids, polyacrylonitrile, nylons and cellulose, in addition to polyesters, fluorinated polymers, and polyurethanes as listed above. Desirably, the textile strands comprise one or more polymers that do not require treatment or modification to be biocompatible. More desirably, the textile strands comprise biocompatible polyesters. Even more desirable, textile strands comprise polyethylene terephthalate and PTFE. A preferred commercial example of polyethylene terephthalate especially suitable for weaving is Dacron. These materials are inexpensive, easy to handle, have good physical characterstics and are suitable for clinical application.

Materials used for the metal strands need only be biocompatible or able to be made biocompatible. Suitable materials for the metal strands include stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber.

In one example, the metal strands comprise shape memory metals. Suitable shape memory metals include, for example, TiNi (Nitinol), CuZnAl, and FeNiAl alloys. Particularly preferred are "superelastic" metal alloys. Superelasticity refers to a shape memory metal alloy's ability to spring back to its austenitic form from a stress-induced martensite at temperatures above austenite finish temperature. The austenite finish temperature refers to the temperature at which the transformation of a shape memory metal from the martensitic phase to the austenitic phase completes.

For example, martensite in a nitinol alloy may be stress induced if stress is applied at a temperature above the nitinol alloy's austenite start temperature. Since austenite is the stable phase at temperatures above austenite finish temperature under no-load conditions, the material springs back to its original shape when the stress is removed. This extraordinary elasticity is called superelasticity. In one example, nitinol wire may be in the superelastic condition where the wire has been cold worked at least 40% and given an aging heat treatment at approximately 500 degrees Celsius for at least 10 minutes. The nitinol wire is in its fully superelastic condition where the use temperature is greater than the austenite finish temperature of the nitinol wire.

The graft may be primarily woven of a single textile strand material or combination of textile strand materials. Determination of which combination of materials woven in which direction of the graft that is most appropriate may be based on the type of clinical application, properties of the graft that are desired, and further factors such as the weave type, textile strand properties such as the size or denier of the textile strands, finishing techniques, and/or permeability of the graft. For example, for percutaneous application, thin grafts are preferred. Such thin grafts comprise textile strands that have are fine or have a low denier. Desirably, textile graft strands range in size from about 0.1 denier to about 200 denier.

Alternatively a fabric may be constructed by weaving, knitting or braiding Nitinol alone (i.e. without any polyester). Further this Nitinol fabric can be covered with films, consisting of any plastic material as well as biological material. This can be achieved by, for example, melting interwoven polyester under controlled conditions.

Stents

One or more stents may be attached or adhered to the variable weave graft by any suitable means, including but not limited to welding, stitching, bonding, and adhesives. In one example, stents may be sutured to the variable weave graft. In general, stents for use in connection with the present disclosure typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube).

In one example, stents may be located distal and proximal to a reduced density region. For example, in FIG. 1, stent 100 is located proximal, or upstream, from reduced density region 111, and stent 101 is located distal to the region 111. Stents located distal and proximal to a reduced density region provide structure and rigidity to the variable weave graft. Additionally, proximal and distal stents may seal against the main vessel wall to prevent leakage around a branch vessel following perforation.

In another example, stents are located at the proximal and distal ends of the variable weave graft. For example, in FIG. 2, stents are located at the proximal 201, 206 and distal 204, 205 graft ends. The graft proximal 201 and distal stents 204, 205 may seal against the main vessel wall 215 to prevent undesirable fluid leakage, for example by reducing blood leakage into an aneurysmal sac 221 spanned by an implanted variable weave graft. Additional stents 202, 203 may further aid in sealing against the vessel wall 215 to prevent undesirable fluid leakage into the aneurysmal sac 221.

The stents may be self-expanding or balloon-expandable, and may be deployed according to conventional methodology, such as by an inflatable balloon catheter, by a self-deployment mechanism (after release from a catheter), or by other appropriate means. The stents may be bifurcated, configured for any blood vessel including coronary arteries and peripheral arteries (e.g., renal, superficial femoral, carotid, and the like), a urethral stent, a biliary stent, a tracheal stent, a gastrointestinal stent, or an esophageal stent, for example. In one example, the stent is a vascular stent such as the commercially available Gianturco Z-stent from Cook Incorporated (Bloomington, Ind.).

The stents may be made of one or more suitable biocompatible materials such as stainless steel, nitinol, MP35N, gold, tantalum, platinum or platinum irdium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the stents comprise stainless steel or nitinol.

Radiopacity

Also provided are examples where the variable weave graft comprises a means for orienting the graft within a body lumen. For example, reduced density textile graft regions may be marked for radiographic visualization to facilitate precise alignment of each reduced density region with the particular branch anatomical conduit (e.g., carotid, innominate, subclavian, intercostal, superior mesenteric, celiac, renal, iliac, hypogastric, or visceral vessels). Radiopaque portions of the textile graft would be seen by remote imaging methods including X-ray, ultrasound, Magnetic Resonance Imaging and the like, or by detecting a signal from or corresponding to the marker.

Figure 5A:
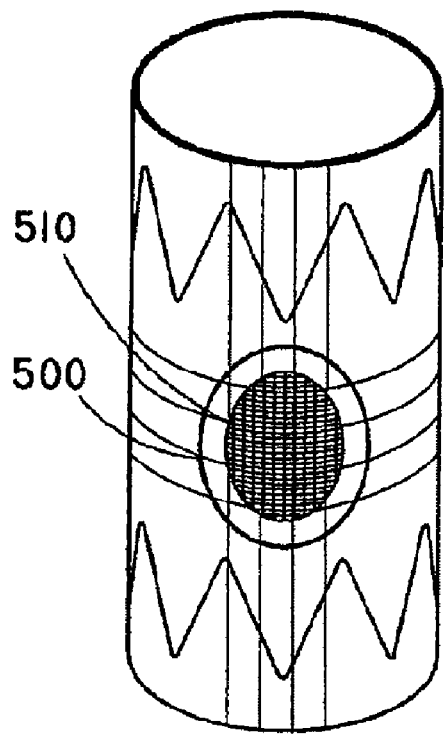
FIGS. 5A and 5B are perspective illustrations of variable weave grafts having radiopaque markers about a reduced density region.
Figure 5B:
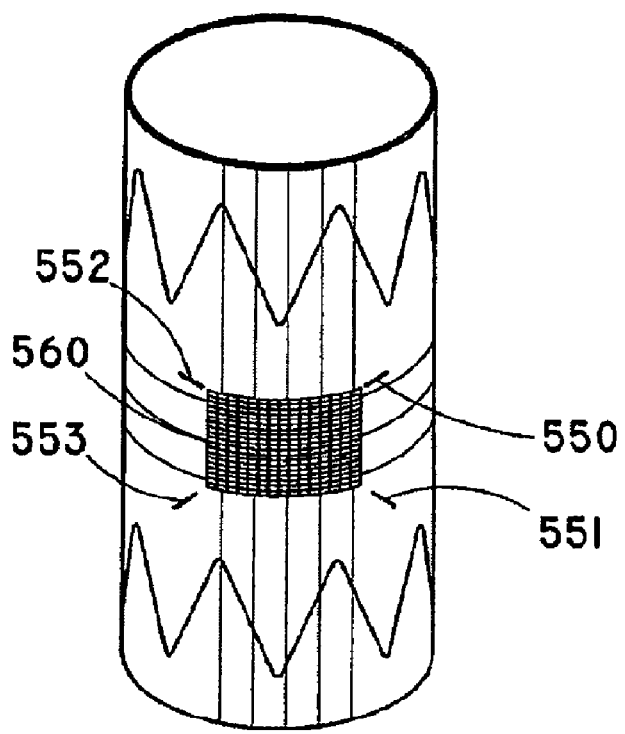

FIGS. 5A and 5B illustrate various examples comprising radiopaque markers to facilitate tracking and positioning of the variable weave graft. In FIG. 5A, a radiopaque ring 500 circumscribes the graft reduced density region 510. FIG. 5B illustrates four radiopaque markers 550, 551, 552, 553 located adjacent a reduced density region 560. Alternatively, stents located proximal and distal a reduced density region may comprise radiopaque portions to assist in appropriately orienting the variable weave graft in the body vessel.

In other examples, the delivery device can comprise indicia relating to the orientation of the variable weave graft and reduced density region(s) within the body vessel. In other examples, indicia can be located, for example, on a portion of a delivery catheter that can be correlated to the location of the graft within a body vessel.

Radiopaque materials may be added to the graft by any fabrication method or absorbed into or sprayed onto the surface of part or all of the graft. The degree of radiopacity contrast can be altered by implant content. Common radiopaque materials include barium sulfate, bismuth subcarbonate, and zirconium dioxide. Other radiopaque elements include: cadmium, tungsten, gold, tantalum, bismuth, platium, iridium, and rhodium. Radiopacity is typically determined by fluoroscope or x-ray film.

Attachment of Graft in Body Vessel

Variable weave grafts according to the present disclosure may optionally include supplemental attachment means such as anchoring members, suturing, stapling, searing, bonding, gluing, bioadhesives, or otherwise adhering the medical device to the vessel wall or combinations thereof. For example, the variable weave graft may be secured in place with one or more anchoring devices.

A wide variety of structural features are acceptable for use in grafts as anchoring members, and any suitable structural feature can be used. For example, individual barbs may be used to implant the variable weave graft into a body vessel. The barbs may be secured to the graft by any means known to one skilled in the art, including but not limited to welding to included stents, stitching, bonding, and adhesives. Desirably, barbs may be attached to stents included in the graft. In some examples, the number, arrangement, and configuration of barbs can vary according to design preference and the clinical use of the variable weave graft. The barbs can have any suitable shape, including points or "fish hook"-like configurations. The barbs may or may not penetrate the vessel wall, depending on their design and other factors.

Alternatively or in addition to anchoring members, bioadhesives may be used for attachment. Bioadhesive may be included in any suitable part of the prosthesis. Preferably, the bioadhesive is attached to the abluminal surface of the variable weave graft. Selection of the type of bioadhesive, the portions of the prosthesis comprising the bioadhesive, and the manner of attaching the bioadhesive to the graft can be chosen to perform a desired function upon implantation. For example, the bioadhesive can be selected to promote increased affinity of the desired portion of graft to the section of the body vessel against which it is urged.

Bioadhesives for use in conjunction with the present disclosure include any suitable bioadhesives known to those of ordinary skill in the art. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta(TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinyl-pylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivitized with sticky molecules such as arginine, glycine, and aspartic acid, and copolymers.

Furthermore, commercially available bioadhesives that may be used in the present disclosure include, but are not limited to: FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Bioactive Agents

Optionally, the graft can include one or more bioactive agents. The bioactive agent can be included in any suitable part of the graft. The bioactive materials can be attached to the graft in any suitable manner. For example, a bioactive agent may be sprayed onto the graft material, or stents may be dipped in bioactive agent. Selection of the type of bioactive agent, the portions of the graft comprising the bioactive agent, and the manner of attaching the bioactive agent to the graft can be chosen to perform a desired function upon implantation. For example, the bioactive material can be selected to treat indications such as coronary artery angioplasty, renal artery angioplasty, carotid artery surgery, renal dialysis fistulae stenosis, or vascular graft stenosis.

The bioactive agent can be selected to perform one or more desired biological functions. For example, the abluminal surface of the graft can comprise a bioactive selected to promote the ingrowth of tissue from the interior wall of a body vessel, such as a growth factor. An anti-angiogenic or antineoplastic bioactive such as paclitaxel, sirolimus, or a rapamycin analog, or a metalloproteinase inhibitor such as batimastat can be incorporated in or coated on the graft to mitigate or prevent undesired conditions in the vessel wall, such as restenosis. Many other types of bioactive agents can be incorporated in the graft.

Bioactive materials for use in biocompatible coatings include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Delivery of Variable Weave Graft

The variable weave graft can be configured for delivery to a body vessel. For example, a prosthesis comprising a variable weave graft according to the present disclosure and stents can be compressed to a delivery configuration within a retaining sheath that is part of a delivery system, such as a catheter-based system. Upon delivery, the prosthesis can be expanded, for example, by inflating a balloon from inside the stents. The delivery configuration can be maintained prior to deployment of the prosthesis by any suitable means, including a sheath, a suture, a tube or other restraining material around all or part of the compressed prosthesis, or other methods.

Prostheses can be deployed in a body vessel by means appropriate to their design. Prostheses of the present disclosure can be adapted for deployment using conventional methods known in the art and employing percutaneous transluminal catheter devices. The prostheses are designed for deployment by any of a variety of in situ expansion means.

In one example, a prosthesis comprising self-expanding stents and a variable weave graft of the present disclosure may be mounted onto a catheter that holds the prosthesis as it is delivered through the body lumen and then releases the prosthesis and allows it to self-expand into contact with the body lumen. This deployment is effected after the prosthesis has been introduced percutaneously, transported transluminally and positioned at a desired location by means of the catheter. The self-expanding prosthesis may be deployed according to well-known deployment techniques for self-expanding medical devices. For example, the prosthesis may be positioned at the distal end of a catheter with a removable sheath or sleeve placed over the prosthetic valve to hold the prosthesis in a contracted state with a relatively small diameter. The prosthesis may then be implanted at the point of treatment by advancing the catheter over a guide wire to the location of the lesion, aligning reduced yarn density regions with any branch vessels, and then withdrawing the sleeve from over the prosthesis. The stent graft will automatically expand and exert pressure on the wall of the blood vessel at the site of treatment.

The guide wire may be used to perforate reduced density regions, thereby creating fenestrations to provide blood flow to branch vessels. Metal strands reinforce the fenestration and aid in reducing blood leakage. The catheter, sleeve, and guide wire may then be removed from the patient.

In some examples, a stent such as a bridge stent or covered stent is deployed through the perforated fenestrations to assist blood flow to branch vessels. Metal strands may assist the graft in forming a tighter structure around the bridge stent deployed through the perforation, thereby reducing blood loss.

In some examples, a bioabsorbable suture or sheath can be used to maintain a self-expanding stent graft in a compressed configuration both prior to and after deployment. As the bioabsorbable sheath or suture is degraded by the body after deployment, the prosthesis can expand within the body vessel. In some examples, a portion of the prosthesis can be restrained with a bioabsorbable material and another portion allowed to expand immediately upon implantation. For example, a self-expanding stent graft can be partially restrained by a bioabsorbable material upon deployment and later expand as the bioabsorbable material is absorbed.

In another example, a stent graft may be first positioned to surround a portion of an inflatable balloon catheter. The prosthesis, with the balloon catheter inside is configured at a first, collapsed diameter. The prosthesis and the inflatable balloon are percutaneously introduced into a body vessel, following a previously positioned guide wire. For example, in rapid exchange, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthesis are positioned within the body passageway at the point where the prosthesis is to be placed. Thereafter, the balloon is inflated and the prosthesis is expanded by the balloon portion from the collapsed diameter to a second expanded diameter. After the prosthesis has been expanded to the desired final expanded diameter, the balloon is deflated, reduced yarn density regions are perforated, and the catheter may be withdrawn, leaving the prosthesis in place. The prosthesis may be covered by a removable sheath during delivery to protect both the prosthesis and the vessels.

Figure 6:
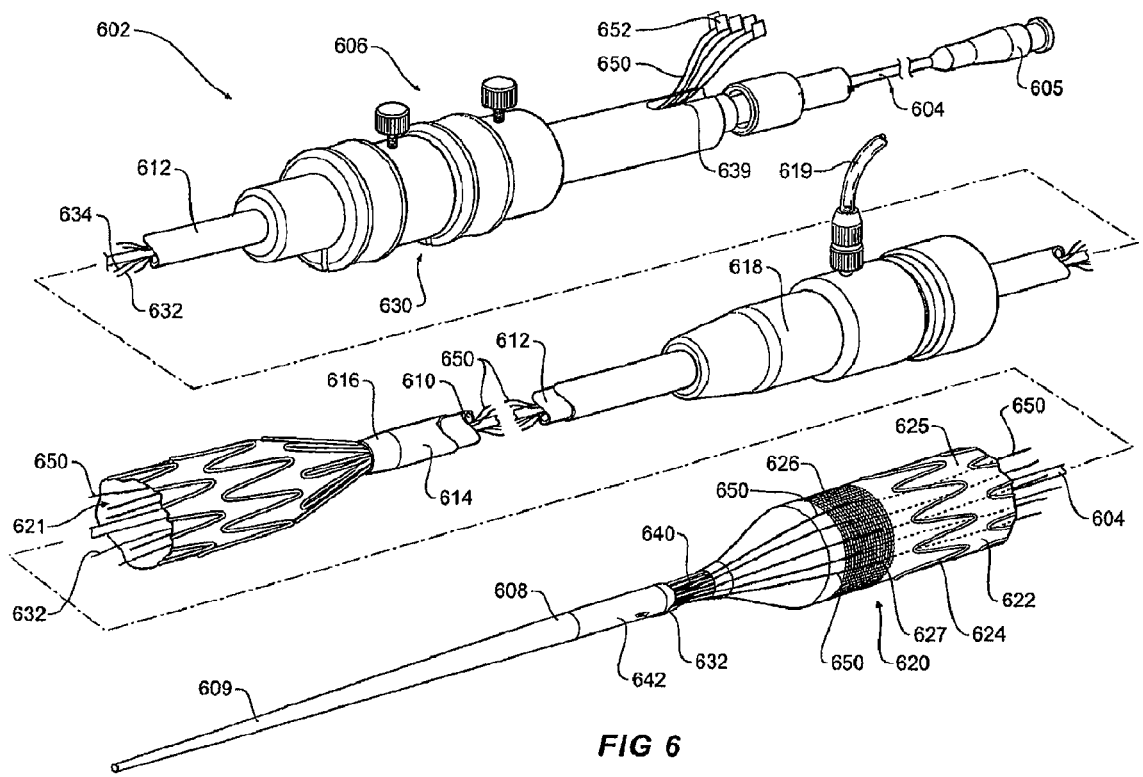
FIG. 6 depicts an example of an implantable prosthesis and a delivery device for the implantable prosthesis.

FIG. 6 depicts one example of a delivery device 602 and implantable prosthesis 620. The delivery device 602 has a guide wire catheter 604 which extends from a distal handle 606 to the proximal tapered nose cone dilator 608 longitudinally through a passageway or lumen 610 of a pusher catheter 612. The pusher catheter is connected to the handle 606 at its distal end. The pusher catheter 612 comprises a relatively thin wall to define the pusher lumen 610 through which a delivery catheter for a side branch stent graft can be deployed. The guide wire catheter also passes through the pusher lumen 610. An introducer sheath 614 fits coaxially around the pusher catheter 612 and extends from a tapered proximal end 616 which optionally includes a radiopaque marker to a connector valve and hub 618 attached to the distal end of the sheath 614. The introducer sheath 614 extends proximally to the nose cone dilator 608 and covers the implantable prosthesis 620, such as a stent graft, during introduction of the deployment device into a patient and is withdrawn in a distal direction to expose the stent graft 620 during deployment when the deployment device is in a selected position within the vasculature of a patient. As illustrated in FIG. 6 the sheath 614 has been retracted to expose the stent graft retained on the delivery device.

Connector valve and hub 618 includes a silicone disk assembly (not shown) for preventing the backflow of fluids therethrough. The disk assembly includes a slit for the insertion of the nose cone dilator 608 and delivery catheter 612. Connector valve and hub 618 also includes side arm 619 to which a tube may be connected for introducing and aspirating fluids therethrough. Nose cone dilator 608 includes a tapered proximal end 609 for accessing and dilating a vascular access site over a well-known and commercially available guide wire (not shown).

The stent graft or implantable prosthesis 620 is carried on the guide wire catheter 604 proximally of the pusher catheter 612 and distally of the nose cone dilator 608. The stent graft or implantable prosthesis 620 comprises a tubular body of a biocompatible material 622 with a graft lumen 621 therethrough and a plurality of self expanding stents 624. The stent graft 620 also comprises at least a portion of the lumen being defined by a woven fabric comprising textile strands and metal strands aligned in a first direction interwoven with textile strands and metal strands aligned in a second direction. The woven fabric further comprises a main portion 625 and at least one reduced density region 626. The main portion has a weave density that is greater than the weave density of the reduced density region. The metal strands in the first direction and metal strands in the second direction are interwoven in at least the reduced density region.

A male Luer lock connector hub 605 is attached at the distal end of the guide wire catheter 604 for connection to syringes and other medical apparatus. The handle 606 at the distal end of the pusher catheter 612 remains outside a patient in use and carries trigger wire release handle mechanisms 630 which are used to release the various portions of the stent graft.

The proximal end the stent graft 620 is retained on the delivery device by the use of trigger wires 632 connected to one of the release handles 630 and the distal end of the stent graft is retained on the delivery device by the use of a trigger wire 634 connected to another of the release handles 630.

In this example the implantable prosthesis or stent graft 620 includes a proximal exposed stent 640 which during delivery is received into a capsule 642 at the distal end of the nose cone dilator 608. Other forms of retention of the proximal and distal ends of the stent graft onto the delivery device are also within the scope of the disclosure.

The delivery device also includes a number of indwelling guide wires 650. The guide wires enter into the pusher catheter 612 at the handle 606 through a port 639 and extend proximally through the pusher lumen 610 of the pusher catheter into the graft lumen 621 and then proximally within the stent graft towards the proximal end of the stent graft. The guide wire 650 pass through the wall of the tubular body in the region of reduced density weave 626 at a range of exit positions 627 as will be discussed in more detail below. Marker tags 652 at the distal ends of the guide wires 650 enable a physician to know which guide wire corresponds to a selected position of exit of the respective guide wire in the region of reduced density weave 626.

In use of the delivery device of this example, a guide wire is inserted in a vessel of the human or animal body with an introducer needle using, for example, the percutaneous vascular access Seldinger technique. The guide wire is introduced up the vessel to a site for deployment of the implantable prosthesis 620. The delivery device 602 is then introduced over the guide wire through to the vessel to the site for deployment of the implantable prosthesis 620. The implantable prosthesis is positioned so that the region of reduced density weave 626 is adjacent to a branch artery, for example a branch artery which is to be catheterised. For instance in the case of a descending aorta it may the renal arteries that are to be catheterised. These branch arteries can be in a range of positions both circumferentially and longitudinally in the aorta. Once the implantable prosthesis has been positioned suitable radiographic techniques can be used to determine the position of the renal arteries and a respective one of the plurality of indwelling guide wires 650 can be selected and the other ones removed by pulling on the respective tags 652. A dilator can then be introduced over the selected guide wire 650 and used to make and enlarge a fenestration in the region of reduced weave density.

A suitable side arm delivery catheter can then be used to deploy a side arm stent graft or stent assembly into the side branch artery by entry at the port 639 and extending through the pusher lumen 610. In a first stage a pointed tip dilator in a dilator catheter may be introduced over the selected guide wire and used to form an initial aperture of fenestration at the exit point in the region of reduced density weave. The dilator catheter can be left in place while the dilator is withdrawn and a suitable guide wire to catheterise the branch artery deployed through the dilator catheter and the branch artery catheterised. Once the main stent graft has been placed in its final position and the proximal and distal ends released a side arm stent graft can be deployed into the branch artery.

Hence it will be seen that placement of a number of the guide wires 650 through the wall of the tubular body in the region of reduced density weave 626 at a range of positions enables a suitable guide wire 650 (or suitable wires) to be selected which most nearly corresponds to the position of a branch artery to facilitate catheterisation of the branch artery. The remaining guide wires 650, extending through the wall of the tubular body in the region of reduced density weave 626, can be retracted.

Figure 7A:
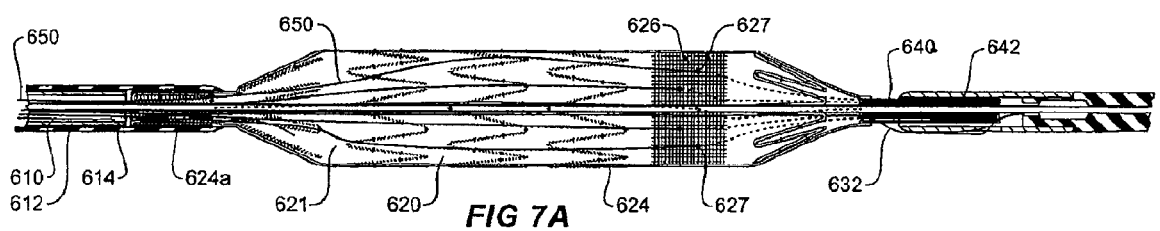
FIGS. 7A and 7B depict certain aspects of the implantable prosthesis and delivery device for the implantable prosthesis as shown in FIG. 6.
Figure 7B:
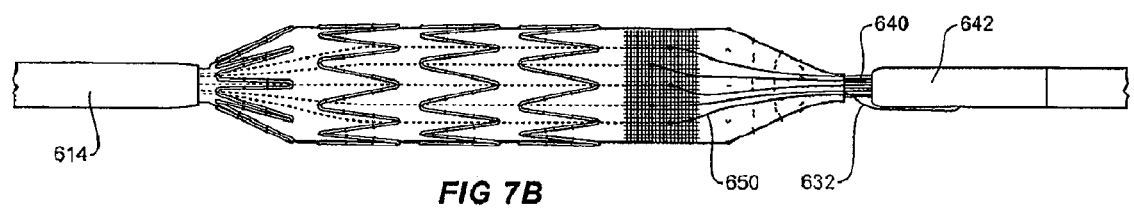

FIGS. 7A and 7B depict detailed aspects of the implantable prosthesis and delivery device for the implantable prosthesis as shown in FIG. 6. (e.g., in FIGS. 7A and 7B those items corresponding to items in FIG. 6 have the same reference numerals.) FIG. 7A shows a longitudinal cross sectional view of part of the delivery device and the implantable prosthesis of FIG. 6. FIG. 7B depicts a view of a portion of the delivery device and the implantable prosthesis of FIG. 6.

In FIG. 7A it will be noted that the sheath 614 has been retracted to the extent that the region of reduced density 626 has been exposed and several stents distal of the region but that the terminal distal stent 624a is still held in a retracted form to enable control of the stent graft 620. The indwelling guide wires 650 pass through the pusher lumen 610 of the pusher catheter 612 and enter the lumen 621 of the stent graft 602 before passing through the wall of the stent graft in the region of reduced density weave 626. In this example the stent graft does not have a self expanding stent in the region of reduced density weave.

After the guide wires 650 pass outside the stent graft 620, as can particularly seen in FIG. 7B, they extend proximally and are receive into the capsule 642 at the distal end of the nose cone dilator 608 along with the proximal exposed stent 640.

Figure 8:
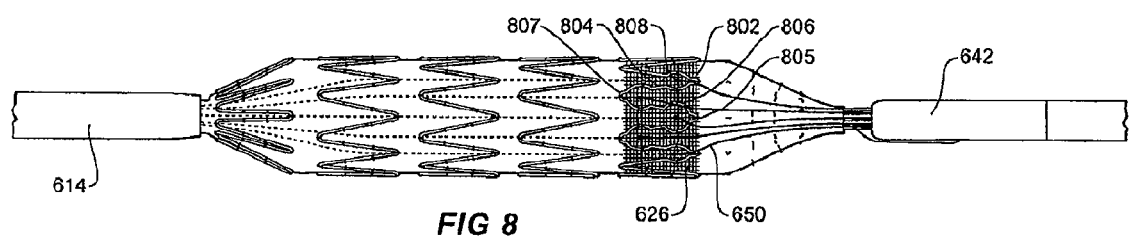
FIG. 8 depicts a further example of an implantable prosthesis and delivery device for the implantable prosthesis.

FIG. 8 depicts detailed aspects of an alternative example of an implantable prosthesis and delivery device for the implantable device. In FIG. 8 those items corresponding to items in FIG. 6 have the same reference numerals. The implantable prosthesis of FIG. 8 comprises a self expanding stent 802 in the region of reduced density weave 626. The stent comprises struts 804 and proximal bends 805 and distal bends 807. The struts 804 of the stent 802 between the bend 805 and 807 have been bent into semicircles 806 in the plane of the notional cylindrical surface of the stent around and away from each of the exit points 808 of the guide wires 650. This structure provides assistance as a reinforcement around a fenestration if one is made at the respective exit point 806.

While various aspects and examples have been described, it will be apparent to those of ordinary skill in the art that many more examples and implementations are possible within the scope of the disclosure. Accordingly, the disclosure is not to be restricted except in light of the attached claims and their equivalents.

We claim:

1. An implantable prosthesis for treatment of a main vessel defect near one or more branch vessels, the prosthesis comprising:
   a graft fabric comprising textile strands aligned in a first direction interwoven with textile strands and metal strands aligned in a second direction, the woven strands defining a lumen with a proximal end and a distal end, a main portion having a first area and at least one passage disposed between the proximal and distal end and having a second area smaller than the first area;
   where at least some of the metal strands are woven in at least the main portion and bound the at least one passage; and
   where, although at least some textile strands traverse the at least one passage, the at least one passage is defined by having a lower weave density than the main portion.

2. The prosthesis of claim 1, further comprising at least two stents attached to the graft fabric, one of which is attached between the distal end and the at least one passage, the other of which is attached between the proximal end and the at least one passage.

3. The prosthesis of claim 1, further comprising metal strands aligned in the first direction interwoven with the textile strands and metal strands aligned in the second direction.

4. The prosthesis of claim 1, where the textile strands aligned in the first direction comprise warp yarns, and the textile strands and metal strands aligned in the second direction comprise weft yarns.

5. The prosthesis of claim 1, where at least one of the metal strands at least partially traverses the at least one passage.

6. An implantable prosthesis comprising:
   a graft body forming a lumen with a proximal end and a distal end;
   where at least a portion of the lumen is defined by a woven fabric comprising textile strands and metal strands aligned in a first direction interwoven with textile strands and metal strands aligned in a second direction;
   where the woven fabric further comprises a main portion having a first area and at least one reduced density region disposed between the proximal end and the distal end of the graft body and having a second area smaller than the first area;
   where the main portion and the least one reduced density region each have a weave density, where the weave density of the main portion is greater than the weave density of the at least one reduced density region;
   where at least some of the metal strands aligned in the first and second directions are interwoven in at least the main portion and bound the at least one reduced density region.

7. The prosthesis of claim 1, where the at least one reduced density region is round, obround, polygonal, rectangular, square, or freeform, or combinations thereof.

8. The prosthesis of claim 1, where the lumen has a circumference and the at least one reduced density region comprises a circumferential width which is less than the circumference of the lumen.

9. The prosthesis of claim 1, where the textile strands and metal strands aligned in the first direction comprise warp strands, and the textile strands and metal strands aligned in the second direction comprise weft strands.

10. The prosthesis of claim 9, where the main portion comprises between about 50 and about 300 weft textile strands per inch and between about 50 and about 300 warp textile strands per inch and where the at least one reduced density region comprises between about 10 and about 200 weft textile strands per inch and between about 10 and about 200 warp textile strands per inch.

11. The prosthesis of claim 9, where the main portion comprises 150 weft textile strands per inch and 250 warp textile strands per inch and where the at least one reduced density region comprises between about 20 and about 50 weft textile strands per inch.

12. The prosthesis of claim 1 where the at least one reduced density region has a perimeter and the metallic strands abut the perimeter of the at least one reduced density region and do not traverse the at least one reduced density region.

13. The prosthesis of claim 1, where at least one of the metal strands at least partially traverses the at least one reduced density region.

14. The prosthesis of claim 1, further comprising a first stent attached near the graft body proximal end and second stent attached near the graft body distal end.

15. The prosthesis of claim 1, further configured to include a plurality of indwelling guide wires disposed within and extending through the graft body at the at least one reduced density region.

16. The prosthesis of claim 15, further comprising a self expanding stent supporting the region of reduced density region, the self expanding stent comprising proximal and distal bends and struts between the proximal and distal bends, the struts being bent into semicircles in the notional cylindrical surface of the stent around and away from exit points of the guide wires thereby providing reinforcement around a fenestration if one is made at the respective exit point.

17. An implantable prosthesis comprising:
a graft body forming a lumen with a proximal end and a distal end;
where at least a portion of the lumen is defined by a woven fabric comprising textile strands and metal strands aligned in a first direction interwoven with textile strands and metal strands aligned in a second direction;
where the woven fabric further comprises a main portion having a first area and at least one reduced density region disposed between the proximal end and the distal end of the graft body and having a second area smaller than the first area;
where the main portion and the least one reduced density region each have a weave density, where the weave density of the main portion is greater than the weave density of the at least one reduced density region;
where at least some of the metal strands aligned in the first and second directions are interwoven in at least the main portion and bound the at least one reduced density region, and
where the at least one reduced density region comprises a perimeter region and a center region within the perimeter region, where the perimeter region comprises a first weave density of interwoven textile strands and the center region comprises a second weave density of interwoven textile strands, where the first weave density is greater than the second weave density.

18. An implantable prosthesis comprising:
a graft body forming a lumen with a proximal end and a distal end;
where at least a portion of the lumen is defined by a woven fabric comprising textile strands and metal strands aligned in a first direction interwoven with textile strands and metal strands aligned in a second direction;
where the woven fabric further comprises a main portion having a first area and at least one reduced density region disposed between the proximal end and the distal end of the graft body and having a second area smaller than the first area;
where the main portion and the least one reduced density region each have a weave density, where the weave density of the main portion is greater than the weave density of the at least one reduced density region;
where at least some of the metal strands aligned in the first and second directions are interwoven in at least the main portion and bound the at least one reduced density region,
where the at least one reduced region comprises a perimeter region and a center region within the perimeter region, where the perimeter regions comprises a first weave density comprising metal strands interwoven with textile strands and the center region comprises a second weave density comprising metal strands interwoven with textile strands, where the first weave density is greater than the second weave density.

* * * * *

UNITED STATES PATENT AND TRADEMARK OFFICE
CERTIFICATE OF CORRECTION

PATENT NO. : 8,353,943 B2  Page 1 of 1
APPLICATION NO. : 12/542336
DATED : January 15, 2013
INVENTOR(S) : Shyam Kuppurathanam et al.

It is certified that error appears in the above-identified patent and that said Letters Patent is hereby corrected as shown below:

In the Claims

In column 16, claim 7, line 57, after "prosthesis of claim" replace "1," with --6,--.

In column 16, claim 8, line 60, after "prosthesis of claim" replace "1," with --6,--.

In column 16, claim 9, line 64, after "prosthesis of claim" replace "1," with --6,--.

In column 17, claim 12, line 13, after "prosthesis of claim" replace "1," with --6,--.

In column 17, claim 13, line 17, after "prosthesis of claim" replace "1," with --6,--.

In column 17, claim 14, line 20, after "prosthesis of claim" replace "1," with --6,--.

In column 17, claim 15, line 23, after "prosthesis of claim" replace "1," with --6,--.

In column 17, claim 16, line 28, after "supporting the region of" insert --at least one--.

Signed and Sealed this
Fourteenth Day of May, 2013

Teresa Stanek Rea
*Acting Director of the United States Patent and Trademark Office*